(12) United States Patent
Adams

(10) Patent No.: US 6,916,332 B2
(45) Date of Patent: Jul. 12, 2005

(54) ENDOLUMINAL FUNDOPLICATION DEVICE AND RELATED METHOD FOR INSTALLING TISSUE FASTENER

(75) Inventor: Ronald Adams, Holliston, MA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 619 days.

(21) Appl. No.: 09/863,666

(22) Filed: May 23, 2001

(65) Prior Publication Data

US 2004/0162567 A9 Aug. 19, 2004

(51) Int. Cl.[7] .............................................. A61B 17/08
(52) U.S. Cl. ..................... 606/219; 606/75; 227/175.1
(58) Field of Search ................................ 606/139, 138, 606/219, 220, 217, 75, 104, 142, 151, 157, 188, 205; 227/51, 53, 175, 181, 19, 178, 175.1, 175.3, 178.1

(56) References Cited

U.S. PATENT DOCUMENTS

| | | | |
|---|---|---|---|
| 5,166,787 A | 11/1992 | Irion | 358/98 |
| 5,549,621 A | 8/1996 | Bessler et al. | 606/151 |
| 5,554,169 A * | 9/1996 | Green et al. | 606/219 |
| 5,571,116 A | 11/1996 | Bolanos et al. | 606/139 |
| 5,897,562 A * | 4/1999 | Bolanos et al. | 606/139 |
| 5,906,625 A * | 5/1999 | Bito et al. | 606/142 |
| 6,086,600 A | 7/2000 | Kortenbach | 606/139 |
| RE37,814 E * | 8/2002 | Allgeyer | 606/219 |
| 6,461,363 B1 * | 10/2002 | Gadberry et al. | 606/139 |
| 6,743,239 B1 * | 6/2004 | Kuehn et al. | 606/139 |

FOREIGN PATENT DOCUMENTS

| | | | | |
|---|---|---|---|---|
| WO | WO 00/78227 A1 | 12/2000 | | A61B/17/064 |
| WO | WO 02/28289 A1 | 4/2002 | | A61B/17/072 |

* cited by examiner

*Primary Examiner*—Henry Bennett
*Assistant Examiner*—Andrea M. Ragonese
(74) *Attorney, Agent, or Firm*—Finnegan Henderson Farabow Garrett & Dunner, L.L.P.

(57) ABSTRACT

A distal assembly of an endoscopic surgical device, and a related method, having a first arm and a second arm pivotal relative to the first arm. Each arm is configured to hold a part of a two-part fastener at a distal end of the arm. A closing mechanism is positioned proximate a proximal end of each of the first and second arms opposite the distal end of each of the first and second arms. The closing mechanism is configured to move in relation to the first and second arms so as to close over at least one of the first and second arms to cause the distal ends of the arms to come together. An actuation member is also attached to the closing mechanism actuable to cause the closing mechanism to move in relation to the first and second arms.

13 Claims, 5 Drawing Sheets

ENDOLUMINAL FUNDOPLICATION DEVICE AND RELATED METHOD FOR INSTALLING TISSUE FASTENER

DESCRIPTION OF THE INVENTION

1. Field of the Invention

The invention relates to an endoscopic surgical instrument. More particularly, the invention relates to a flexible instrument for transoral invagination and fundoplication of the stomach to the esophagus.

2. Background of the Invention

Gastroesophageal reflux occurs when stomach acid enters the esophagus. This reflux of acid into the esophagus occurs naturally in healthy individuals, but also may become a pathological condition in others. Effects from gastroesophageal reflux range from mild to severe. Mild effects include heartburn, a burning sensation experienced behind the breastbone. More severe effects include a variety of complications, such as esophageal erosion, esophageal ulcers, esophageal stricture, abnormal epithelium (e.g., Barrett's esophagus), and/or pulmonary aspiration. These various clinical conditions and changes in tissue structure that result from reflux of stomach acid into the esophagus are referred to generally as Gastro-esophageal Reflux Disease (GERD).

Many mechanisms contribute to prevent gastroesophageal reflux in healthy individuals. One such mechanism is the functioning of the lower esophageal sphincter (LES). The LES is a ring of smooth muscle and increased annular thickness existing in the last four centimeters of the esophagus. In its resting state, the LES creates a region of high pressure (approximately 15–30 mm Hg above intragastric pressure) at the opening of the esophagus into the stomach. This pressure essentially closes the esophagus contents of the stomach cannot pass back into the esophagus. The LES opens in response to swallowing and peristaltic motion in the esophagus, allowing food to pass into the stomach. After opening, however, a properly functioning LES should return to the resting, or closed state. Transient relaxations of the LES do occur in healthy individuals, typically resulting in occasional bouts of heartburn.

The physical interaction occurring between the gastric fundus and the esophagus also prevents gastroesophageal reflux. The gastric fundus is a lobe of the stomach situated at the top of the stomach distal to the esophagus. In asymptomatic individuals, the fundus presses against the opening of the esophagus when the stomach is full of food and/or gas. This effectively closes off the esophageal opening to the stomach and helps to prevent acid reflux back into the esophagus. More specifically, as the food bolus is immersed in gastric acid, it releases gas which causes the fundus of the stomach to expand and thereby put pressure on the distal esophagus causing it to collapse. The collapse of the esophagus lumen reduces the space for the stomach acid to splash past the closed esophagus lumen and thereby protect the proximal esophagus from its destructive contact.

In individuals with GERD, the LES functions abnormally, either due to an increase in transient LES relaxations, decreased muscle tone of the LES during resting, or an inability of the esophageal tissue to resist injury or repair itself after injury. These conditions often are exacerbated by overeating, intake of caffeine, chocolate or fatty foods, smoking, and/or hiatal hernia. Avoiding these exacerbating mechanisms helps curb the negative side effects associated with GERD, but does not change the underlying disease mechanism.

A surgical procedure has been developed to prevent acid reflux in patients whose normal LES functioning has been impaired. This procedure, a Nissen fundoplication, involves bringing the fundus into closer proximity to the esophagus and suturing the fundus thereto, to help close off the esophageal opening into the stomach. Traditionally, this procedure has been performed as an open surgery, but also has been performed laparoscopically.

As with any surgery, the attendant risks are great. The Nissen fundoplication is a very difficult procedure to complete and thus the patient is anesthitized for a long time. Due to relatively large incisions necessary in the performance of open surgery, relatively large amounts of blood are lost, the risk of infection increases and the potential for post-operative hernias is high.

A laparoscopic procedure may involve performing laparotomies for trocar ports (penetrations of the abdominal wall) percutaneous endoscopic gastronomies (incisions through the skin into the stomach) and the installation of ports through which, for example, a stapler, an endoscope, and an esophageal manipulator (invagination device) are inserted. Under view of the endoscope, the esophageal manipulator is used to pull the interior of the esophagus into the stomach. When the esophagus is in position, with the fundus of the stomach plicated, the stapler is moved into position around the lower end of the esophagus and the plicated fundus is stapled to the esophagus. The process may be repeated at different axial and rotary positions until the desired fundoplication is achieved. This procedure is still relatively invasive requiring incisions through the stomach, which has a risk of infection. The location of the incision in the abdominal wall presents a risk of other negative effects, such as sepsis which can be caused by leakage of septic fluid contained in the stomach.

Less invasive treatments of gastroesophageal reflux disease may utilize a remotely operable invagination device and a remotely operable surgical stapler, both of which are inserted transorally through the esophagus. The invagination device may be inserted first and used to clamp the gastroesophageal junction. The device is then moved distally, pulling the clamped gastroesophageal junction into the stomach, thereby invaginating the junction and involuting the surrounding fundic wall. The stapler then may be inserted transorally and delivered to the invaginated junction where it is used to staple the fundic wall. The stapling device must apply sufficient force to pierce the tissue that is to be fastened.

SUMMARY OF THE INVENTION

In accordance with one aspect of the invention, a distal assembly of an endoscopic surgical device is provided having a first arm and a second arm pivotal relative to the first arm. Each arm is configured to hold a part of a two-part fastener at a distal end of the arm. A closing mechanism is positioned proximate a proximal end of each of the first and second arms opposite the distal end of each of the first and second arms. The closing mechanism is configured to move in relation to the first and second arms so as to close over at least one of the first and second arms to cause the distal ends of the arms to come together. An actuation member is also attached to the closing mechanism and is actuable to cause the closing mechanism to move in relation to the first and second arms.

According to another aspect of the invention, a tissue fastening tool is utilized with an endoscope. The endoscope is provided with a stop mechanism to come in contact with the distal assembly and stop the distal assembly at a predetermined location along the endoscope.

According to yet another aspect of the invention, an endoscope may be provided with a housing that contains two light and imaging systems, one facing in a distal direction and the other facing in a proximal direction opposite the distal direction.

Another aspect of the invention includes a method for fasting tissue that includes guiding a tissue fastening tool along an endoscope until the tissue fastening tool contacts a stop mechanism so as to position the tissue fastening tool relative to the endoscope. The tissue fastening tool has a pair of arms and each of the arms holds a part of a two-part fastener. The operator then positions the pair of arms about the tissue to be fastened and the arms are then closed to deploy the two-part fastener and fasten the tissue.

According to another aspect, the invention includes a method for fastening tissue that includes guiding a tissue fastening tool through a body lumen to tissue to be fastened. The tissue fasting tool includes a pair of arms, each arm holding a part of a two-part fastener. The pair of arms is then positioned about the tissue to be fastened. A closing mechanism is then actuated to close over at least one of the arms to cause the arms to come together and the parts of the two-part fastener to mate and fasten the tissue.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims. The foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate embodiments of the invention and together with the description, serve to explain the principles of the invention.

DESCRIPTION OF THE PREFERRED EMBODIMENTS

Reference will now be made in detail to the present preferred and exemplary embodiments of the invention, examples of which are illustrated in the accompanying drawings. Wherever possible, the same reference numbers will be used throughout the drawings to refer to the same or like parts.

Figure 1:
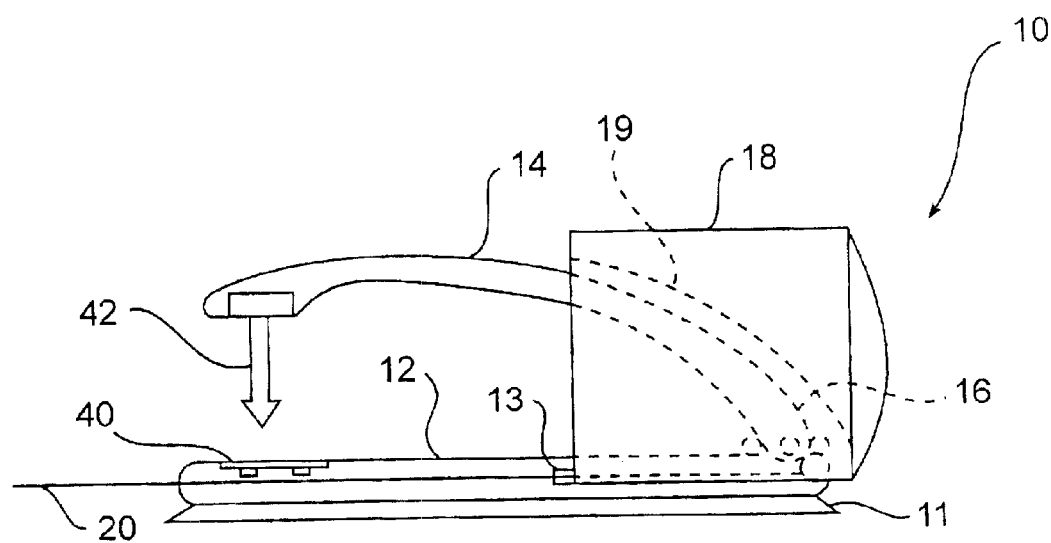
FIG. 1 is a plan view of a distal end of a fastener application tool according to an embodiment of the present invention.
Figure 2A:
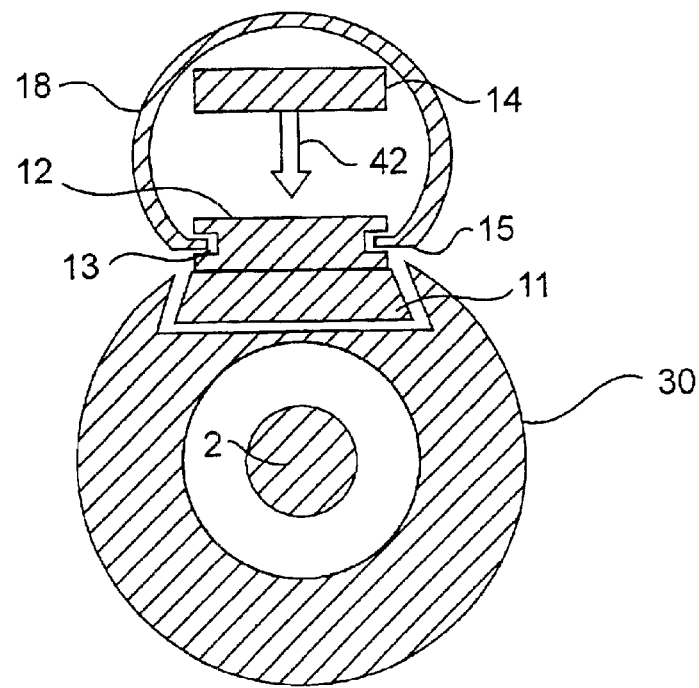
FIG. 2A is a cross-sectional view along line A—A of the fastener application tool of FIG. 2 that has been rotated 90° from the orientation shown in FIG. 2.

FIG. 1 shows a distal end of a tissue fastener application tool 10 according to an embodiment of the present invention. In this figure, tool 10 is in an intermediate position between a fully open position and a deployed position where the tool deploys a fastener to secure a tissue fold. Tool 10 preferably is used endoscopically, by insertion transorally through the esophagus, to fasten the fundic wall with a tissue fastener. Tool 10 includes a pair of pivot arms 12, 14 configured to pivot about a pivot point 16 located at a proximal end of arms 12, 14. Beneath arm 12 is located flange 11. Flange 11 is preferably shaped to fit into a groove located within sleeve 30 (shown in FIG. 2A). This flange and groove is depicted in FIG. 2A as a dove-tail joint, but may be any other mating configuration known in the art. At a distal end of arm 12 is a holding mechanism for holding a female part 40 of a two-part tissue fastener. Likewise, at the distal end of arm 14 is a holding mechanism to hold a male part 42 of the two-part tissue fastener. The female and male fastener parts 40,42 could be located on either pivot arm and are not intended to be limited to the configuration disclosed in the drawings. The two-part tissue fastener and its holding mechanisms may take the form of any suitable tissue fastener and holding mechanism known in the art, including, for example, holding mechanisms that include storage for housing multiple fastener parts.

Tool 10 further includes a closing tube 18 positioned over the proximal end of pivot arms 12,14 where the arms intersect at pivot point 16. A spring device may be located at pivot point 16 to supply a spring force to normally hold arms 12,14 in an open position when closing tube 18 is in a retracted position, such as that shown in FIG. 3. Arm 12 preferably is in a fixed position relative to tube 18 and arm 14 rotates from an open position (FIG. 3) to a closed position (FIG. 4) relative to arm 12. Tube 18 is hollow to accommodate arms 12,14 and the full span of rotation of arm 14.

Closing tube 18 is connected to an elongate actuator, such as a cable 20, which connects to a proximal actuator (not shown) of any suitable type well known in the art, so that a user may pull a proximal end of cable 20 that is outside the patient, or actuate a proximal actuator to do so, to pull tube 18 toward the distal ends of pivot arms 12,14 and thus over arms 12,14. This causes arm 14 to pivot at point 16 and towards arm 12 to cause fastener parts 40,42 to mate and secure a tissue fold. Arm 12 is provided with a channel 13 into which the base of closing tube 18 rests. This channel, along with a matching protrusion 15 (FIG. 2A) provided at the base of closing tube 18 provides a path along which closing tube may move to facilitate the closing action that brings arms 12 and 14 together to deploy fastener parts 40 and 42.

Pivot arm 14 is preferably curved as depicted in the drawings so as to allow closing tube 18 to close more easily and apply sufficient force to the fastener parts. Also, the inside of closing tube 18 may be provided with a cam surface 19 that is substantially the same shape as arm 14 to act as a cam and provide an even greater closing force to be applied to arms 12 and 14. Arm 14, however, may be straight or have any other suitable configuration. In addition, arm 12 may be arranged so that it pivots toward arm 14 when tube 18 is closed. The arrangement of the distal end of the tool 10 provides a high mechanical advantage on the arms to produce a sufficient closing force.

Figure 2:
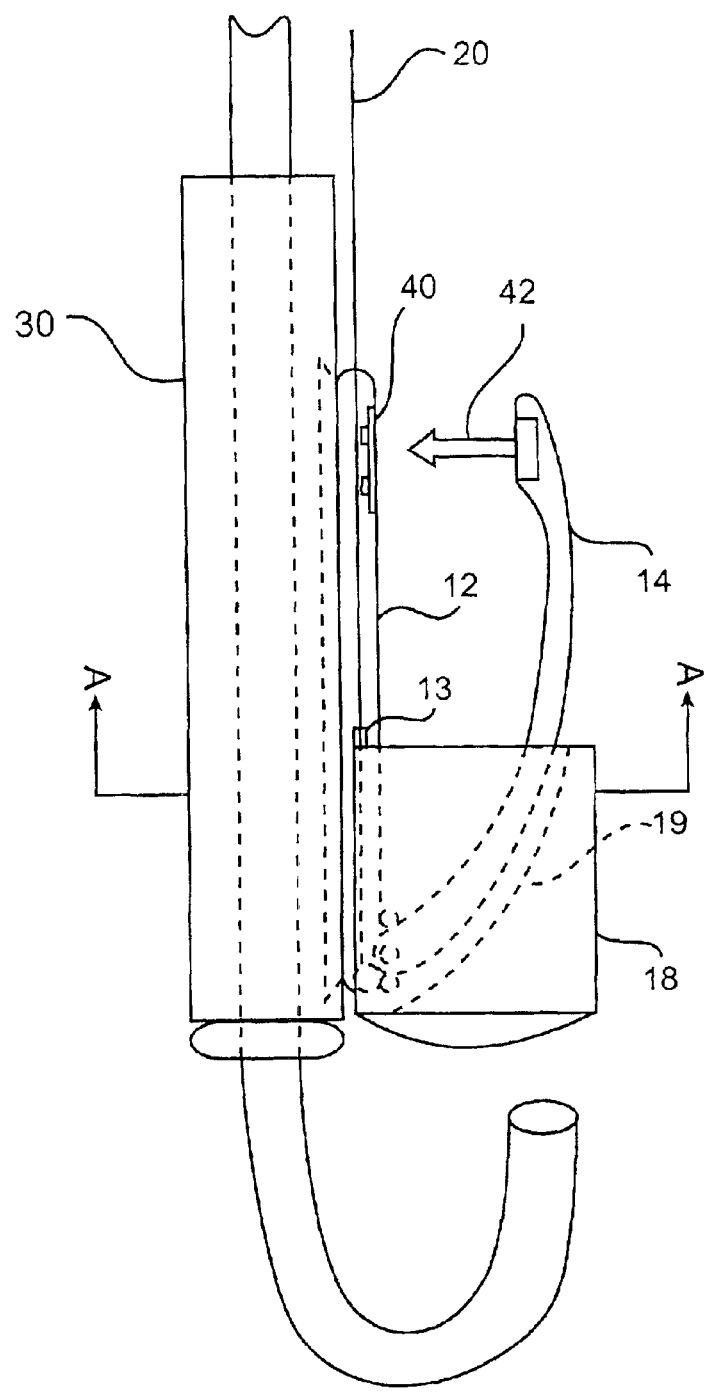
FIG. 2 is a view of the fastener application tool of FIG. 1 affixed to a sleeve and in place over an endoscope.
Figure 3:
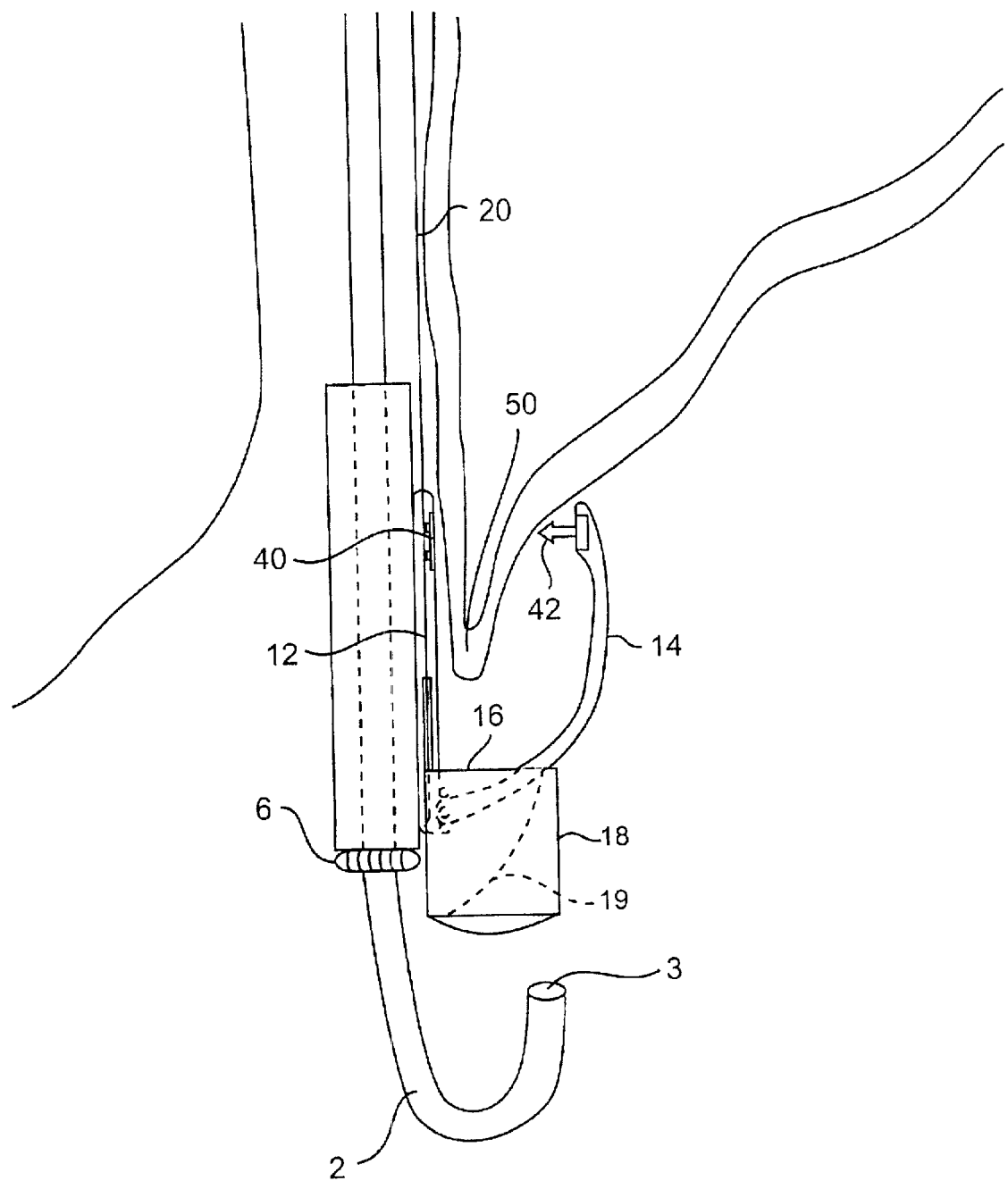
FIG. 3 is a view of the fastener application tool of FIG. 1 in place over an endoscope and having a stop ring to accurately position the tool for performing the surgical procedure.
Figure 4:
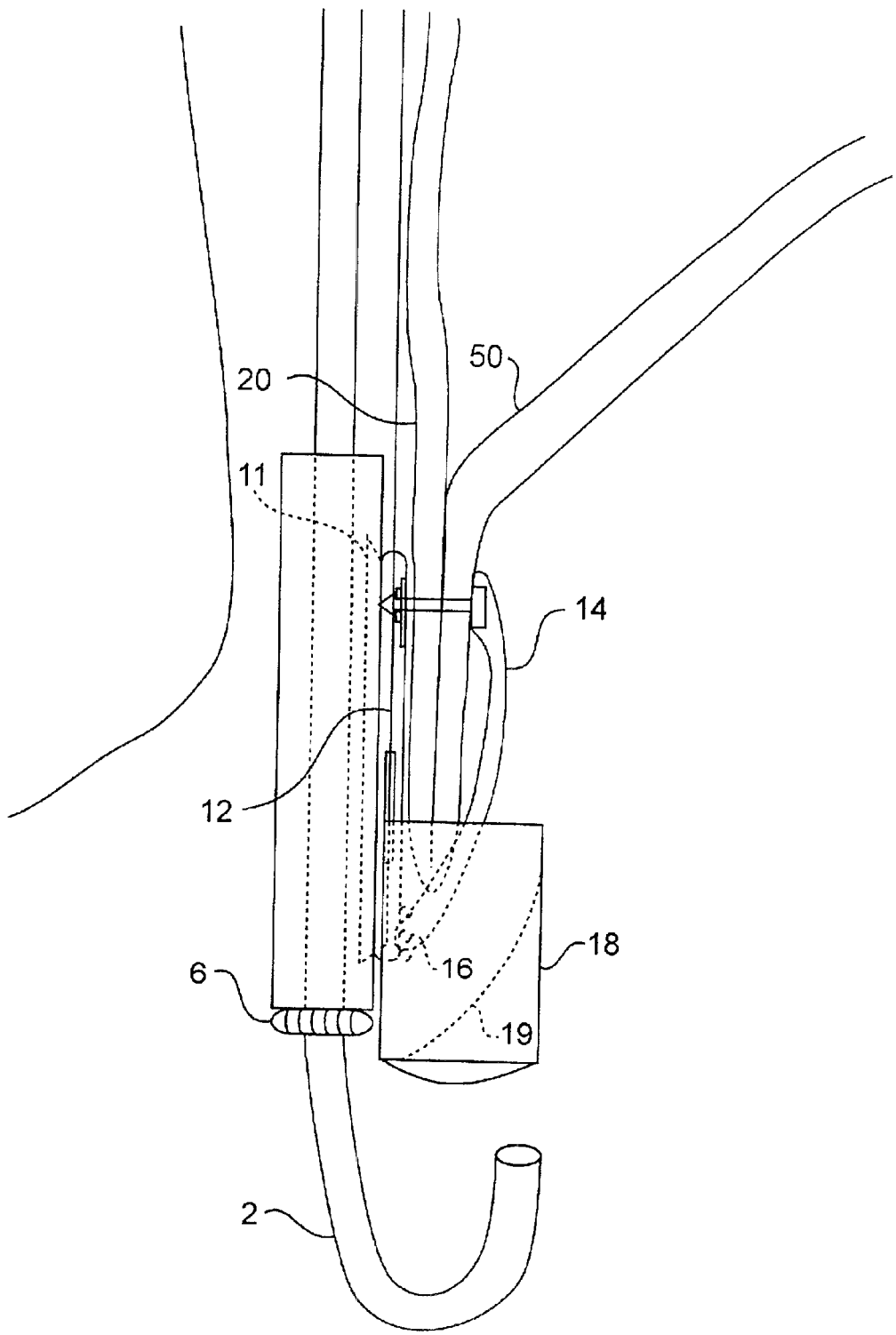
FIG. 4 is a view showing the fastener application tool and endoscope of FIG. 2, with the tool in a deployed position inserting a fastener through the tissue.

Tissue fastener application tool 10 preferably is used in combination with an endoscope, such as an endoscope 2 according to an embodiment of the present invention and shown in FIGS. 2, 3, and 4. Endoscope 2 preferably is a small diameter endoscope that incorporates features needed for the surgical procedure, for example visualization (including imaging and a light source), insufflation, and/or steerability. Additional endoscope features, such as working channels for a biopsy device, may be eliminated so that the endoscope size is reduced, permitting the tissue fastener application tool to pass adjacent the endoscope within the lumen of the esophagus. Endoscope 2 may be approximately 3 mm in diameter, for example and include a light source 3 at its distal end that is capable of illuminating the upper gastrointestinal region. Endoscope 2 may also include an appropriate steering mechanism so that the distal end of the endoscope may be turned 180 degrees upon entry into the stomach, as shown in FIGS. 2, 3, and 4.

Figure 5:
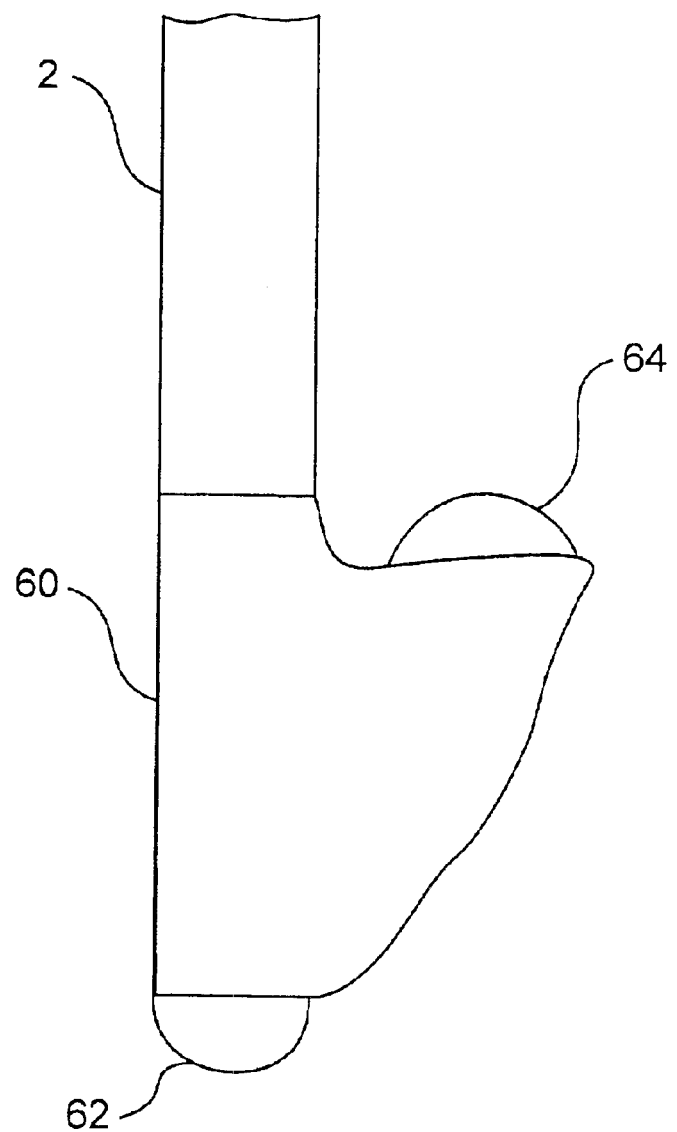
FIG. 5 is a plan view of a distal end of an endoscope according to an embodiment of the present invention.

In another embodiment shown in FIG. 5, endoscope 2 may include alternative light and imaging/camera assembly 60. Rather than requiring the endoscope to curve around at the distal end through use of a steering mechanism, endoscope 2 could have light and imaging/camera assembly 60, in the form of a housing, at the distal end that allows both forward viewing as endoscope 2 is inserted into the stomach as well as rearward viewing to allow the operator to see the procedure once endoscope 2 is in the proper position. Assembly 60 may include a standard camera and light source 62 pointing away from the distal end of assembly 60 and also a second camera and light source 64 that branches off of endoscope 2 and points rearward (or proximally) toward the tool to be used in the procedure. A user may switch imaging and light through a suitable switch at the proximal end outside the patient between these forward and rearward views. This configuration allows for a streamlined endoscope and does not require the operator to change the position of the distal end of endoscope 2 to bring it from a forward pointing position during insertion to a rearward pointing position during the procedure.

In an embodiment, endoscope 2 may be used as a guide, like a guide wire, for the insertion of the tissue fastener application tool, as will be explained. Endoscope 2 also may include a stop, such as that shown in FIGS. 2, 3, and 4, in the form of, for example, a ring 6 configured to set the position of tool 10 relative to endoscope 2.

In operation, and according to an embodiment of a method of the present invention, endoscope 2 is inserted transorally, through the esophagus, and into the stomach. Endoscope 2 is manipulated so that the imaging and light source is in a position to view the esophagus and upper portions of the stomach, as shown in FIGS. 2, 3, and 4. If an endoscope having a distal assembly as shown in FIG. 5 is used, camera and light source 64 is switched on to view those portions of the gastrointestinal tract. The tissue fastener application tool 10 then is inserted into the esophagus along endoscope 2.

As tool 10 is inserted through the esophagus and into the stomach, arms 12,14 preferably are in a closed position. Tool 10 is inserted until a portion of the distal end of sleeve 30 abuts against stop ring 6 of endoscope 2 so that tool 10 is at an appropriate position relative to endoscope 2 and its imaging and light assembly. Once tool 10 is in position, tube 18 is moved over arms 12,14 and towards the proximal ends of arms 12, 14 to rotate arm 14 to an open position away from arm 12. Endoscope 2 and tool 10 can then be moved proximally as a unit so that arms 12,14 are opened about a tissue fold 50 that is to be fastened together, as shown in FIG. 3.

During insertion, cable 20 is actuated to keep tube 18 over arms 12,14 to maintain this closed position. Because tool 10 is preferably in a closed position during insertion, a spring may be provided in channel 13 that would bias tube 18 into an open position once cable 20 is released. Once the tool is in position, the operator may pull cable 20, thus causing closing tube 18 to move toward the distal ends of arms 12,14. As tube 18 moves closer to the distal ends of arms 12,14, force is applied until the two fastener parts 40, 42 are brought together in a mated position as seen in FIG. 4. As closing tube 18 is actuated by pulling cable 20, it will counteract the force of the spring at pivot 16 and bring pivot arms 12, 14 together to mate the fastener parts 40,42.

According to an embodiment of the this invention, tube 18 may include an alternative assembly for closing arms 12,14. Instead of cable 20 being used to pull closing tube 18 to cause pivot arms 12,14 to close, cable 20 may be replaced with a flexible shaft having a threaded distal end that is inserted into a threaded hole in tube 18. In this configuration, the flexible shaft is rotated in one direction to cause the threaded portions of both the shaft and closing tube 18 to work together to draw closing tube 18 toward the distal ends of pivot arms 12,14 to cause fastener parts 40,42 to mate. Cable 20 may then be rotated in the opposite direction to move closing tube 18 distally away from arms 12, 14, thus allowing arms 12, 14 to move apart again. Tube 18 may include any other suitable alternative actuation mechanism that moves tube 18 over arms 12,14.

Other embodiments of the invention will be apparent to those skilled in the art from consideration of the specification and practice of the invention disclosed herein. The specification and examples are exemplary only, with a true scope and spirit of the invention being indicated by the following claims.

What is claimed is:

1. A distal assembly of an endoscopic surgical device, comprising:

a first arm and a second arm pivotal relative to the first arm, each arm configured to hold a part of a two-part fastener at a distal end of the arm;

a closing mechanism positioned proximate a proximal end of each of the first and second arms opposite the distal end of each of the first and second arms, the closing mechanism configured to move in relation to the first and second arms and contact an outer surface of at least one of the first and second arms that faces away from the other of the first and second arms to cause the distal ends of the arms to come together; and an actuation member attached to the closing mechanism actuable to cause the closing mechanism to move in relation to the first and second arms.

2. The distal assembly of claim 1, wherein the actuation member is a cable.

3. The distal assembly of claim 1, wherein each of the first and second arms is straight.

4. The distal assembly of claim 1, wherein one of the first and second arms is curved.

5. The distal assembly of claim 4, wherein the closing mechanism is configured to close over the curved arm.

6. The distal assembly of claim 1, further comprising a spring at a pivot between the first and second arms.

7. The distal assembly of claim 6, wherein the spring provides a force to cause the distal ends of the arms to be pushed apart.

8. The distal assembly of claim 1, wherein the actuation member includes an elongate member having a threaded end that mates with a threaded hole in the closing mechanism.

9. The distal assembly of claim 1, wherein the closing mechanism includes a tube.

10. An assembly for endoscopically deploying a two-part fastener, comprising:

a flexible endoscope;

the distal assembly of claim 1, the distal assembly configured to be guided along the endoscope; and a stop mechanism located on the endoscope and configured to stop the advancement of the distal assembly at a location relative to the endoscope.

11. The assembly of claim 10, wherein the stop mechanism includes a ring.

12. The assembly of claim 10, wherein the endoscope further comprises a distal assembly including a housing having a first light source and imaging system facing a distal direction and a second light source and imaging system facing a proximal direction opposite the distal direction.

13. A distal assembly of an endoscope, comprising:

a housing having a first light source and imaging system facing a distal direction and a second light source and imaging system facing a proximal direction opposite the distal direction.

* * * * *

UNITED STATES PATENT AND TRADEMARK OFFICE
CERTIFICATE OF CORRECTION

PATENT NO. : 6,916,332 B2
DATED : July 12, 2005
INVENTOR(S) : Ronald D. Adams

It is certified that error appears in the above-identified patent and that said Letters Patent is hereby corrected as shown below:

<u>Column 8,</u>
Line 6, "A distal assembly of an endoscope, comprising:" should read -- The distal assembly of claim 1, further comprising: --.

Signed and Sealed this

Thirtieth Day of August, 2005

JON W. DUDAS
*Director of the United States Patent and Trademark Office*